(12) United States Patent
Iyengar et al.

(10) Patent No.: US 11,719,687 B2
(45) Date of Patent: Aug. 8, 2023

(54) ANALYTE DETECTION METER AND ASSOCIATED METHOD OF USE

(71) Applicant: AgaMatrix, Inc., Salem, NH (US)

(72) Inventors: Sridhar Iyengar, Salem, NH (US); Ian Harding, Wells (GB); Richard Williams, Somerville, MA (US); Kevin Cai, Acton, MA (US)

(73) Assignee: AgaMatrix, Inc., Salem, NH (US)

( * ) Notice: Subject to any disclaimer, the term of this patent is extended or adjusted under 35 U.S.C. 154(b) by 539 days.

(21) Appl. No.: 16/222,683

(22) Filed: Dec. 17, 2018

(65) Prior Publication Data

US 2019/0113498 A1 Apr. 18, 2019

Related U.S. Application Data (63) Continuation of application No. 13/835,672, filed on Mar. 15, 2013, now Pat. No. 10,168,313.

(51) Int. Cl.
*G01N 33/487* (2006.01)
*G01N 27/327* (2006.01)

(52) U.S. Cl.
CPC ... *G01N 33/48771* (2013.01); *G01N 27/3274* (2013.01)

(58) Field of Classification Search
CPC . G01N 33/48771; G01N 27/327–3274; G01N 33/48707; G01N 33/48785; G01N 33/48792; G01N 33/49; A61B 5/14532; A61B 5/1468; A61B 5/1477; A61B 5/1486

See application file for complete search history.

(56) References Cited

U.S. PATENT DOCUMENTS

| | | | |
|---|---|---|---|
| 4,476,149 A | 10/1984 | Poppe et al. |
| 4,714,874 A | 12/1987 | Morris et al. |
| 4,929,426 A | 5/1990 | Bodai et al. |
| 5,243,516 A | 9/1993 | White |

(Continued)

FOREIGN PATENT DOCUMENTS

| | | |
|---|---|---|
| CA | 2 811 712 A1 | 5/2021 |
| CN | 1839314 A | 9/2006 |

(Continued)

OTHER PUBLICATIONS

International Search Report from priority application No. PCT/US2014/016452 dated May 9, 2014.

(Continued)

*Primary Examiner* — Maris R Kessel
(74) *Attorney, Agent, or Firm* — Larson & Anderson, LLC (57) ABSTRACT

A method for obtaining information encoded on an electrochemical test strip is provided. The test strip has two electrodes disposed within a sample space and the information is encoded on the test strip prior to introduction of liquid sample. The method includes the step of introducing sample to the sample space so that the sample is in contact with the two electrodes within the sample space. In another step a value is determined that is representative of the double layer capacitance of the test strip and/or the equivalent capacitance of the test strip. The determined value is then translated into information reflecting a characteristic of the test strip prior to introduction of sample.

9 Claims, 4 Drawing Sheets

(56) References Cited

U.S. PATENT DOCUMENTS

| | | |
|---|---|---|
| 5,266,179 A | 11/1993 | Nankai et al. |
| 5,320,732 A | 6/1994 | Nankai et al. |
| 5,352,351 A | 10/1994 | White et al. |
| 5,438,271 A | 8/1995 | White et al. |
| 5,582,697 A | 12/1996 | Ikeda et al. |
| 5,942,102 A | 8/1999 | Hodges et al. |
| 5,997,817 A | 12/1999 | Crismore et al. |
| 6,071,391 A | 6/2000 | Gotoh et al. |
| 6,212,417 B1 | 4/2001 | Ikeda et al. |
| 6,251,260 B1 | 6/2001 | Heller et al. |
| 6,284,125 B1 | 9/2001 | Hodges et al. |
| 6,299,757 B1 | 10/2001 | Feldman et al. |
| 6,616,819 B1 | 9/2003 | Liamos et al. |
| 6,662,439 B1 | 12/2003 | Bhullar |
| 6,743,635 B2 | 6/2004 | Neel et al. |
| 6,872,298 B2 | 3/2005 | Kermani |
| 7,090,764 B2 | 8/2006 | Iyengar et al. |
| 7,344,626 B2 | 3/2008 | Harding et al. |
| 7,501,052 B2 | 3/2009 | Iyengar et al. |
| 7,517,439 B2 | 4/2009 | Harding et al. |
| 7,547,382 B2 | 6/2009 | Harding et al. |
| 7,601,249 B2 | 10/2009 | Iyengar et al. |
| 7,601,299 B2 | 10/2009 | Beaty et al. |
| 7,625,473 B2 | 12/2009 | Hsu |
| 7,645,374 B2 | 1/2010 | Diamond et al. |
| 7,645,421 B2 | 1/2010 | Groll |
| 7,695,608 B2 | 4/2010 | Kim et al. |
| 7,713,392 B2 | 5/2010 | Harding et al. |
| 7,771,583 B2 | 8/2010 | Diamond et al. |
| 2003/0094383 A1 | 5/2003 | Kermani |
| 2003/0098233 A1 | 5/2003 | Kermani et al. |
| 2003/0109798 A1 | 6/2003 | Kermani |
| 2004/0118704 A1* | 6/2004 | Wang ............... G01N 33/48785 205/792 |
| 2005/0019212 A1* | 1/2005 | Bhullar .............. G01N 27/3272 422/400 |
| 2006/0226985 A1 | 10/2006 | Goodnow et al. |
| 2006/0231418 A1 | 10/2006 | Harding |
| 2006/0231424 A1 | 10/2006 | Harding |
| 2007/0068806 A1* | 3/2007 | Yang ................ G01N 33/48771 204/403.01 |
| 2007/0074977 A1 | 4/2007 | Guo et al. |
| 2008/0112852 A1 | 5/2008 | Neel et al. |
| 2008/0267823 A1 | 10/2008 | Wang et al. |
| 2008/0314882 A1 | 12/2008 | Bhuller et al. |
| 2010/0243441 A1* | 9/2010 | Groll ...................... B29C 65/74 204/403.01 |
| 2011/0309846 A1 | 12/2011 | Yamamoto et al. |
| 2012/0080326 A1 | 4/2012 | Chatelier |
| 2012/0142117 A1 | 6/2012 | Ahn et al. |
| 2013/0027064 A1 | 1/2013 | Austera et al. |
| 2018/0059043 A1 | 3/2018 | Leone |

FOREIGN PATENT DOCUMENTS

| | | | |
|---|---|---|---|
| CN | 1975403 A | 6/2007 | |
| CN | 101715555 A | 5/2010 | |
| WO | 2004113909 A1 | 12/2004 | |
| WO | 2006109277 A2 | 10/2006 | |
| WO | WO-2010095787 A1 * | 8/2010 | ....... G01N 33/48771 |
| WO | 2012037486 A1 | 3/2012 | |

OTHER PUBLICATIONS

European Search Report dated Sep. 12, 2019 from related European Patent Application No. 19179521.0.

* cited by examiner

Fig. 2

| Characteristic Info | | Capacitance Value |
|---|---|---|
| Region 1 | ─ ─ ─ ─ ─ ─ ─→ | a to b |
| Region 2 | ─ ─ ─ ─ ─ ─ ─→ | c to d |
| Region 3 | ─ ─ ─ ─ ─ ─ ─→ | e to f |
| ERROR | ─ ─ ─ ─ ─ ─ ─→ | Not a to f |

Fig. 3

| Characteristic Info | | Capacitance Value |
|---|---|---|
| Glucose | ─ ─ ─ ─ ─ ─ ─→ | g to h |
| Ketone | ─ ─ ─ ─ ─ ─ ─→ | i to j |
| Error | ─ ─ ─ ─ ─ ─ ─→ | Not g to j |

Fig. 4

| Characteristic Info | | Capacitance Value |
|---|---|---|
| Calibration 1 | ─ ─ ─ ─ ─ ─ ─→ | j to k |
| Calibration 2 | ─ ─ ─ ─ ─ ─ ─→ | l to m |

Fig. 5

| Characteristic | | Capacitance |
|---|---|---|
| Product I.D. 1 | ----------> | n to o |
| Product I.D. 2 | ----------> | p to q |

Fig. 6

| Characteristic | | Capacitance |
|---|---|---|
| Year 1 | ----------> | r to s |
| Year 2 | ----------> | t to u |

ANALYTE DETECTION METER AND ASSOCIATED METHOD OF USE

BACKGROUND OF THE INVENTION

This application relates to methods for encoding information on an electrochemical test strip as well as methods for, and meters capable of, obtaining information encoded on a test strip.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

Electrochemical test meters are known in the art, for example for the determination of blood glucose levels. See, for example, U.S. Pat. Nos. 7,771,583; 7,645,374; 7,601,249; 7,547,382; 7,517,439; 7,501,052; 7,344,626; 7,090,764; 6,662,439; 6,284,125; 6,071,391; 5,942,102; 5,352,2,351; and 5,243,516, all of which are incorporated herein by reference.

Test strips often have information associated with them, such as, inter alia, calibration information, regional or country coding, product identification, customer identification, assay type (e.g. glucose test strip or ketone test strip), and date of manufacture. PCT Patent Application Ser. No. PCT/US 11/51983 and U.S. Pat. Nos. 7,713,392; 7,695,608; 7,645,421; 7,625,473; 7,601,299; and 4,714,874, which are incorporated herein by reference, provide strips with this, and other types of information, encoded onto the test strip and associated meters and methods for decoding the information from the strip. The challenge for manufacturers is how to encode information on a test strip and how to obtain the coded information in a manner that is cost effective, reliable, safe, and robust. The present invention provides systems and methods to solve these difficulties.

SUMMARY OF THE INVENTION

The present invention provides methods for encoding information on to a test strip as well as methods for, and meters capable of, obtaining the information encoded on an electrochemical test strip. The methods of obtaining the information employ the steps of determining a value indicative of the double layer capacitance or the equivalent capacitance of the test strip after sample introduction. This value can then be translated into information regarding a characteristic of the test strip, which is encoded on the test strip prior to sample introduction.

The present Inventors have found that a strip's double layer and/or equivalent capacitance is a variable that can be controlled/altered so as to encode information on to the test strip. Furthermore, the present Inventor's have found that determining a value indicative of the strip's double layer capacitance or equivalent capacitance when sample is present in the sample space and subsequently translating this value into information reflecting a characteristic of the test strip prior to introduction of sample allows for obtaining the information. The encoded information then can be used in a subsequent analysis or correction step to adjust a calculated value (e.g. value obtained in a determination or detection of analyte) or it can be used to generate and/or display an error result or message to a user.

In a first aspect of the present invention, a method for obtaining information encoded on an electrochemical test strip having at least two electrodes within a sample space is provided. The information is encoded on the strip prior to introduction of sample. The method comprises the steps of:
(a) introducing sample to the a sample space so that the sample is in contact with two electrodes within the sample space;
(b) determining a value that is representative of the double layer capacitance or the equivalent capacitance of the test strip; and
(c) translating the value determined in step (b) into information reflecting a characteristic of the test strip prior to introduction of sample;
thereby obtaining information encoded on the electrochemical test strip.

In a second aspect of the present invention, a method for detecting an analyte in a sample in contact with two electrodes within a sample space of an electrochemical test strip is provided. The test strip has characteristic information encoded thereon prior to introduction of a sample. The method comprises the steps of:
(a) introducing sample to the sample space so that the sample is in contact with two electrodes within the sample space;
(b) determining a value that is representative of the double layer capacitance or the equivalent capacitance of the test strip; and
(c) translating the value determined in step (b) into information reflecting a characteristic of the test strip prior to introduction of sample,
(d) detecting analyte in the sample disposed within the sample space, and
(e) using the characteristic information translated in step (c) to modify a result of step (d).

The invention also provides a meter for receiving an electrochemical test strip having electrodes and providing a determination of an analyte in a sample applied to the electrochemical test strip when received in the meter. The meter comprises:
(a) a housing having an opening for receiving an electrochemical test strip, said test strip having characteristic information encoded thereon;
(b) communications means for receiving input from and communicating a result to a user; and
(c) circuitry for making a determination of double layer capacitance or equivalent capacitance on a test strip having two electrodes within a sample space containing sample received within the meter, circuitry for translating the determined double layer capacitance or equivalent capacitance into information reflecting a characteristic of the test strip prior to introduction of sample; and circuitry for determination of an analyte in a sample within the sample space of the test strip.

In a further aspect of the present invention a measurement system is provided. The system comprises a meter, as described above, and a test strip having two electrodes within a sample space, wherein the test strip is disposed within the slot of the housing of the meter.

DETAILED DESCRIPTION OF THE INVENTION

When a sample space of a test strip is filled with sample, or alternatively when the entirety of the electrodes (or dominant electrode) within the sample space are covered with sample, then a determination of a value representative of the test strip's double layer capacitance or equivalent capacitance can be translated into characteristic information encoded on the test strip prior to sample introduction. Information can be encoded on a test strip by altering variables within the sample space which impact the strip's equivalent and/or double layer capacitance when sample covers the electrodes in the sample space. These variables include: controlling or altering the effective area of the electrodes within the sample space of the test strip; controlling or altering the material of construction of the electrodes; electrode surface modification; controlling or altering the type or concentration of ions (e.g. type and amount of ions such as those present as salts in the reagent); controlling or altering the type or concentration of mediator.

Definitions

As used in the specification and claims of this application, the following definitions should be applied:

(a) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment.

(b) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(c) "double layer" refers to the charged layers which form at a conductor/electrolyte interface as a result of adsorption of ions on the conductor surface causing a localized layer of neutralizing mirror charges in the conductor to form near the solid surface. The double layer is formed at each electrode in an electrochemical test strip when a liquid sample is present in contact with the electrode, whether or not a potential is applied. The amount of charge in a double layer, however, is a function of the electrode potential. The double layer structure behaves essentially as a capacitor.

(d) "double layer capacitance" is the capacitance of a double layer. It may be an integral capacitance, in which case it can be represented by the formula $C_{int}=I\Delta t/\Delta V$ or a differential capacitance, in which case it can be represented by the formula $C_{dif}=I/(dV/dt)$, where I is current, t is time and V is voltage. As described in Harding (U.S. Pat. No. 7,547,382), in some instances the measured double layer capacitance can be dominated by one electrode, for example, if one electrode has a substantially larger area, or where the adsorption of ions of one charge is stronger than ions of the other charge in the sample. Double layer capacitance measured in these instances is within the scope of the invention, although care should be taken where one electrode is dominant that the geometry of filling is such that the double layer capacitance of the dominant electrode is representative of the fill-state of the electrochemical strip. Where double layer capacitance of a test strip is determined, it is preferably determined in accordance with the teachings of U.S. Pat. No. 7,547,382, to Harding et. al which is incorporated herein by reference for all purposes.

(e) "double layer charging" is the process of increasing the charge stored in a double layer as a result of an applied potential. The phrase "double layer charging at the electrodes" refer to charging at both electrodes or at a dominant electrode.

(f) "double layer discharging" is the process of decreasing the charge stored in a double layer as a result of switching off an applied potential. The phrase "double layer discharging at the electrodes" refer to discharging at both electrodes or at a dominant electrode.

(g) "equivalent capacitance" is herein understood to mean the total equivalent capacitance between the electrodes (e.g. across the sample space electrochemical test strip, when electrodes are in contact with sample in the sample space) when potential is applied between the electrodes. The "equivalent capacitance" of the test strip is a combination of the strip's double layer capacitance and the strip's Faradaic capacitance. Where equivalent capacitance is determined, it is preferably determined in accordance with the teachings in either or both of U.S. Pat. No. 6,872,298 and/or U.S. patent application Ser. No. 09/974,597 (Published as US 2003/0098233).

(h) "Faradaic capacitance" as used herein refers to the pseudo-capacitance component of the test strip's equivalent capacitance and is representative of the electrochemical reaction process that occurs on the electrode surface.

(i) "electrochemical test strip" or simply "test strip" refers to a strip having at least two electrodes within a sample space, and any necessary reagents for determination of an analyte in a sample placed between the electrodes. In preferred embodiments, the electrochemical test strip is disposable after a single use, and has electrical connectors for attachment to a separate and reusable meter that contains the electronics for applying potential, analyzing signals and displaying a result. In another embodiment, the electrochemical test strip includes multiple sample spaces and electrodes disposed within those sample spaces. In this later embodiment, the "test strip" can be used multiple times where sample is introduced to one or more at the sample spaces at different times.

(j) "facing electrodes" are a pair of electrodes disposed parallel to but in a separate plane from each other. Some or all of the opposed surfaces of a pair of facing electrodes preferably overlap, such that potential gradients and current flows between the electrodes are in a direction substantially perpendicular to the opposed surfaces. Facing electrodes are distinguished from side-by-side electrodes in which the two electrode surfaces lie in the same plane, and in which potential gradients and current flow is substantially parallel to the surface of the electrodes. The present invention can be used with either facing or side-by-side electrodes, as well as other geometric arrangements.

(k) "information encoded on a test strip" is any type of information which details a characteristic of the test strip that is intentionally, unintentionally, or inherently encoded on a test strip during manufacture or otherwise prior to introduction of a sample to be analyzed. The information is encoded on the test strip prior to introduction of sample to the sample space. Information can be encoded on a test strip by altering variables within the sample space which impact the strip's equivalent and/or double layer capacitance when sample covers the electrodes in the sample space. These variables include: controlling or altering the effective area of the electrodes within the sample space of the test strip; controlling or altering the material of construction of the electrodes; electrode surface modification; controlling or altering the type or concentration of ions (e.g. type and amount of ions such as those present as salts in the reagent); controlling or altering the type or concentration of mediator. Encoding information to the test strip for example can be accomplished by forming electrode(s) within the sample space having specified effective areas during manufacture or can be accomplished as a post production step by altering the effective area of the electrode(s) within the sample space by etching, punching, ablating, scoring, or otherwise removing conductive material from the electrode within the sample space. A non-limiting exemplary list of the type of characteristic information capable of being encoded on a test strip includes: calibration information, regional or country coding, product identification, customer identification, assay type (e.g. glucose test strip or ketone test strip), and date of manufacture.

(l) "obtaining information" is herein understood to mean decoding, reading, translating, retrieving, or otherwise obtaining or ascertaining, the information encoded on the test strip.

(m) "translating" is herein understood to mean using a value determined in one set of steps to provide information about the test strip which is representative of a characteristic of the test strip prior to introduction of sample to the test strip. For example, the determined value which is representative of the double layer capacitance or equivalent capacitance of a test strip, can be reconciled with a lookup table stored in a meter or obtained by a meter. The lookup table can have a range, or ranges, of values which are indicative of various characteristic information of the test strip.

(n) "value representative of double layer capacitance or equivalent capacitance" is herein understood to mean the actual determined capacitance or a separate value which comprises information about the capacitance of the strip (e.g. an electrical signal or some other value).

(o) "effective area of an electrode" is herein understood to mean the conductive portion of an electrode, or the dominant electrode, which is in contact with sample in the sample space and capable of being electrically connected with a meter. The "effective area" includes conductive portions of the electrode which are exposed to sample when present in the sample space. The "effective area" includes the conductive portions which are exposed to sample which lie within the two dimensional planar footprint (e.g. length, width, radius, etc.) as well as conductive portions of the electrode which are exposed to sample which lie within a third dimension (e.g. depth or thickness) such as located in pits, crevices, and/or pores of the electrode.

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

Figure 1:
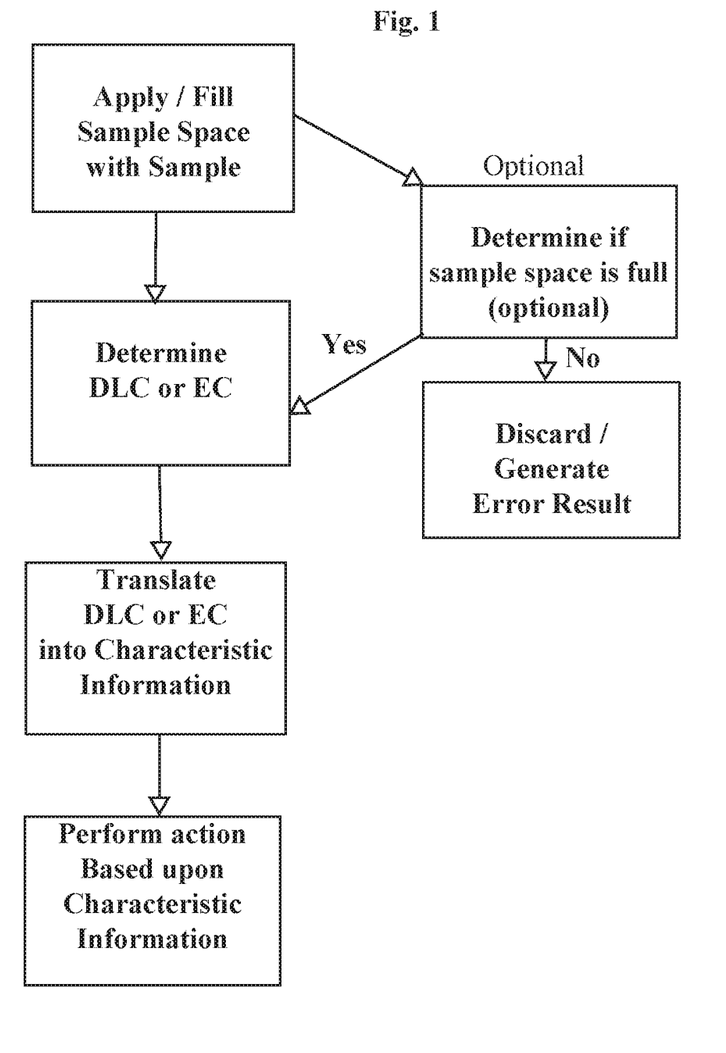
FIG. 1 is a flow chart showing steps of an embodiment of the present invention.

Method of Obtaining Encoded Information from a Test Strip:

In a first aspect, the present invention provides a method for obtaining information encoded on an electrochemical test strip. The test strip has at least two electrodes disposed within a sample space and the information is encoded on the test strip prior to introduction of liquid sample. As shown in FIG. 1, the method comprises the steps of:
(a) introducing sample to the sample space so that the sample is in contact with two electrodes within the sample space;
(b) determining a value that is representative of the double layer capacitance (DLC) or the equivalent capacitance (EC) of the test strip; and
(c) translating the value determined in step (b) into information reflecting a characteristic of the test strip prior to introduction of sample;
thereby obtaining information encoded on the electrochemical test strip.

The step of (b) determining a value that is representative of the double layer capacitance or the equivalent capacitance of the test strip, is known in the art and is not particularly limited herein. The determined value may be the actual value of the test strip's double layer capacitance or its equivalent capacitance, or it may be a value or signal that is representative of either of both of these capacitance values.

Prior art references discussed herein make use of a test strip's double layer capacitance or equivalent capacitance in determining whether a sufficient amount of sample has been applied to and is disposed with the sample space to perform an electrochemical determination of analyte. In these references, it is disclosed that sample volume can be determined as a function of the area of the electrode(s) wetted by sample and the thickness of a spacer layer and/or separation of electrodes. These references each describe and employ different capacitance-determining methods for determining the sample-wetted electrode area within the sample space and hence provide different methods of determining sample sufficiency within the sample space. Any of these methods for determining double layer capacitance or equivalent capacitance can be employed to accomplish step (b) of the present invention.

For example, U.S. Pat. No. 7,547,382, to Harding et. al, which is incorporated herein by reference, discloses several different methods for measuring a test strip's double layer capacitance. Harding uses a measure of the strip's double layer capacitance in a determination of whether sufficient sample is present within the sample space to perform an electrochemical determination of analyte within the sample.

Harding describes that the double layer capacitance of a test strip with sample in the sample space can be determined using the steps of:
(i) applying a potential difference between the electrodes of the test strip;
(ii) switching off the applied potential and optionally reapplying a second potential;
(iii) observing current generated and determining from the observed current a double layer charging or discharging at the electrodes; and
(iv) observing a voltage change after the applied potential is switched off, and
(v) determining the double layer capacitance of the test strip from the measured double layer charging or discharging and the observed voltage change.

Harding employs these steps to determine double layer capacitance of the test strip which is either the integral capacitance or differential capacitance of the test strip.

Where a value representative of the equivalent capacitance of the test strip is determined, it can be determined in accordance with the teachings in either or both of U.S. Pat. No. 6,872,298 and/or U.S. patent application Ser. No. 09/974,597 (Published as US 2003/0098233), both of which list Kermani as an Inventor and are incorporated herein by reference. In these references, Kermani makes use of a test strip's equivalent capacitance when sample is present within the sample space in the determination of whether sufficient sample is present within the sample space to perform an electrochemical determination of analyte within the sample. In US 2003/0098233, Kermani describes a method of determining a test strip's equivalent capacity, includes the steps of:

(i) applying an alternating voltage having a selected amplitude and a selected frequency between the electrodes of the test strip;
(ii) measuring the current generated from the application of potential in step (l); and
(iii) determining the equivalent capacitance of the test strip from the current measured in step (ii), wherein the equivalent capacitance includes both the double layer capacitance and the Faradaic capacitance of the test strip.

In Kermani's U.S. Pat. No. 6,872,298, he describes another method of determining a test strip's equivalent capacity includes the steps of:

(i) applying a potential difference between the electrodes of the test strip thereby charging the test strip, wherein a double layer capacitance is created within the test strip and a voltage is generated by charging the test strip;
(ii) converting the voltage created by charging the test strip to an oscillating voltage having a period proportional to the created double layer capacitance;
(iii) observing the oscillating voltage; and
(iv) determining the equivalent capacitance of test strip from the observed oscillating voltage.

As discussed above, step (b) can be suitably accomplished using the teachings of the prior art and is not particularly limited herein.

To obtain the most accurate (b) determination of a value representative of the strip's double layer capacitance or equivalent capacitance for the purposes of obtaining information encoded on the test strip prior to introduction of sample, the sample space will be preferably completely filled with sample. For example, it is preferred that sample is disposed between and completely covering the electrodes (or dominant electrode). This may mean the sample space is completely filled with sample or this may mean that the sample space is not entirely filled with sample, but that sample covers the electrodes. In preferred embodiment the methods, strips, meters, and meter/strip combinations of the present invention further comprise structures or functionality to determine whether sample completely covers the electrodes (or dominant electrode) within the sample space. This step can occur at any time after introduction of sample, however as shown in FIG. 1 this preferably occurs prior to the determination of the strip's capacitance value. Methods and apparatuses useful for fill detection are well-known in the art and are not particularly limited herein. For example, U.S. Pat. No. 4,929,426 discloses the use of an impedance electrode that sample flows over when the sample chamber is filled, while U.S. Pat. Nos. 5,582,697, 6,212,417, and 6,299,757, all of which are incorporated by reference, disclose the use of a third electrode that can be used for fill detection. U.S. Pat. No. 6,743,635, which is incorporated by reference, discloses a four electrodes approach, including separate fill detect anode and cathode. U.S. Pat. No. 5,997,817, which is incorporated by reference, discloses a test strip with a window through which the sample can be viewed, and a "fill-to-here" line to assess sample sufficiency.

Figure 2:
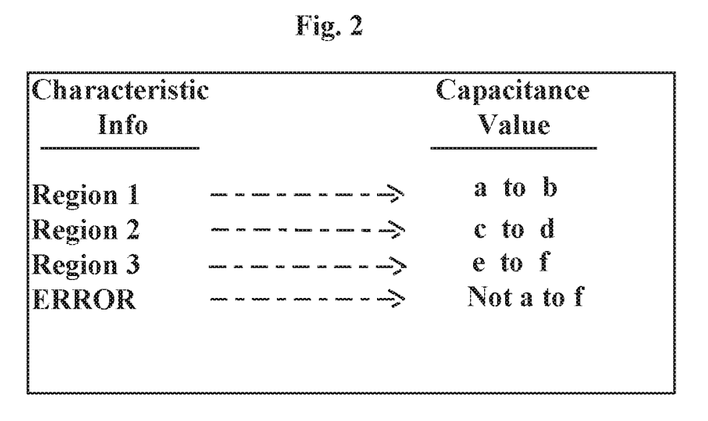
FIGS. 2-6 show different lookup tables containing capacitance values and associated characteristic information.
Figure 3:
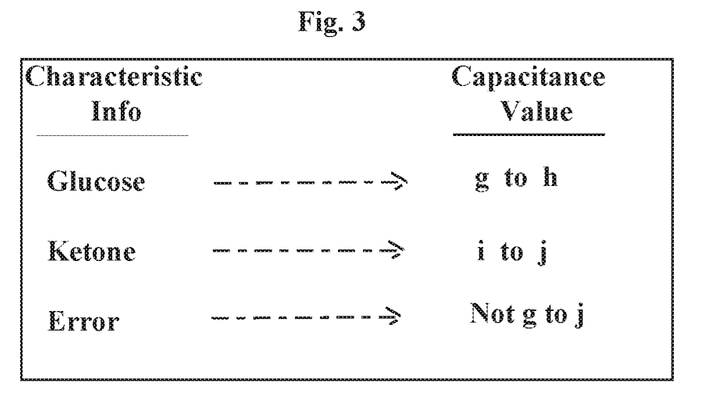
Figure 4:
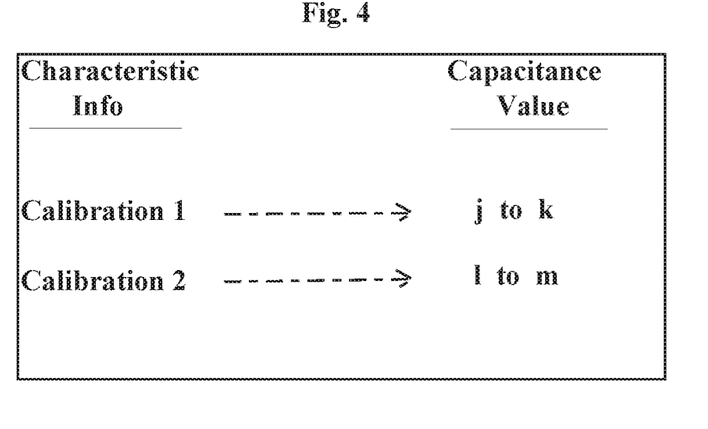
Figure 5:
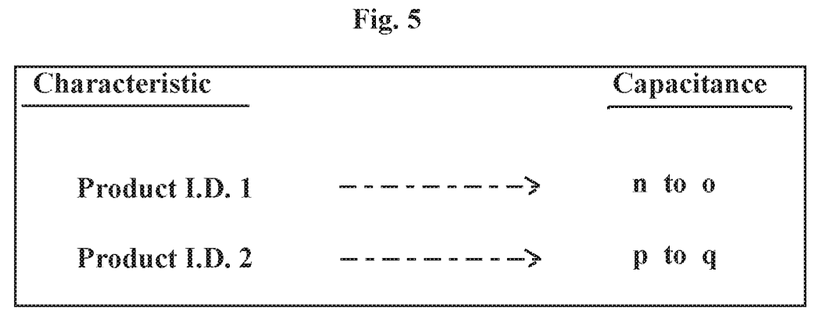
Figure 6:
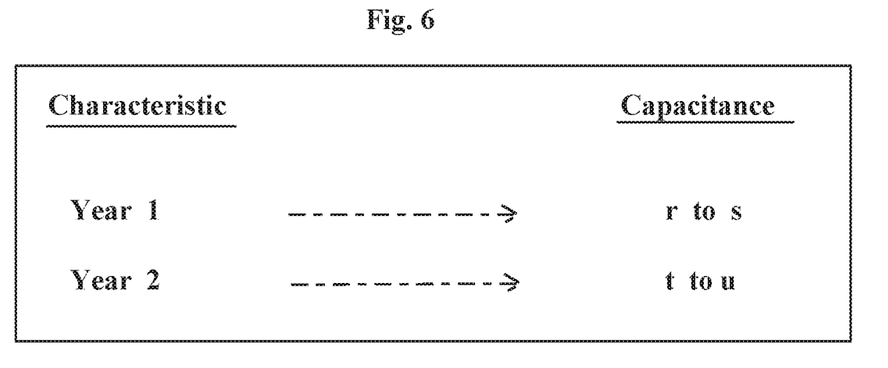

Once the value representative of a test strip's double layer capacitance or equivalent capacitance is determined, this value can be (c) translated into information reflecting a characteristic of the test strip prior to introduction of sample. As shown in FIGS. 2 and 3, the translation step is preferably a reconciliation (e.g. referencing) of the determined double layer capacitance or equivalent capacitance of the test strip with a lookup table. In FIG. 2 the lookup table correlates ranges of capacitance values with regional identification or country coding of the test strips. In FIG. 3, the lookup table correlates ranges of capacitance values with the type of analyte the test strip is designed to measure. In FIG. 4, the lookup table correlates ranges of capacitance values with calibration information of the test strip. In FIG. 5, the lookup table correlates ranges of capacitance values with product identification of the test strip. In FIG. 6, the lookup table correlates ranges of capacitance values with a production or expiration year.

Translating the value of the strip's double layer capacitance or equivalent capacitance into information reflective of a characteristic of the test strip prior to introduction of sample, allows for obtaining useful characteristic information of the test strip. As shown in FIG. 1, in preferred embodiments, the obtained information causes, or is used in, a subsequent action or step. In some embodiments the subsequent action or step is to generate or otherwise cause display of an error result, or error message, which indicates that the test strip is not suitable for use with the meter, or that some other error has occurred. In other embodiments, the subsequent action or step is one where the obtained or translated information is used in a subsequent measurement or analyte determination step or to modify a result from a subsequent measurement or analyte determination step.

Encoding Information on a Test Strip.

Information can be encoded on a test strip by altering variables within the sample space which impact the strip's equivalent and/or double layer capacitance when sample covers the electrodes in the sample space. These variables include: controlling or altering the effective area of the electrodes within the sample space of the test strip; controlling or altering the material of construction of the electrodes; electrode surface modification; controlling or altering the type or concentration of ions (e.g. type and amount of ions such as those present as salts in the reagent); controlling or altering the type or concentration of mediator.

For example in one embodiment when information is to be encoded on a test strip, the effective electrode area may be altered or formed by increasing or decreasing its two-dimensional conductive surface area footprint (e.g. to increase/decrease length, width or radius, etc.) in contact with the sample. Alternatively, or in combination with controlling to two-dimensional surface area footprint, a third conductive dimension of the electrode can be altered/controlled by increasing/decreasing the thickness of the electrode (e.g. where the electrode has a pitted or porous surface which provides a third dimension of sample contact). In other embodiments, the type and/or concentration of mediator and or ions (e.g. salts) present in a reagent disposed within the sample space may be altered to encode information to the test strip, which in turn will alter the strip's double layer and/or equivalent capacitance which allows for translation and obtaining of the information according to the herein described methods.

Determination of an Analyte, for Example Glucose

The methods of the present invention are preferably combined with a subroutine directed to the detection and/or determination of analyte in the sample. The detection and/or determination of analyte subroutine can occur prior to, during, or after obtaining the encoded information from the test strip. In some embodiments, the subroutine of performing and/or the result of the detection and/or determination of analyte is adjusted or corrected depending on the type and content of information obtained from the test strip. In other embodiments the subroutine of detection and/or determination steps is halted, or not performed, depending on the type and content of information obtained from the test strip. In yet other embodiments just a error message is displayed to a user depending on the characteristic obtained from and encoded on the test strip.

Subroutines for the electrochemical detection and determination of an analytes such as glucose are conventionally achieved by applying a potential to an electrochemical cell containing a sample to be evaluated for the presence/amount of glucose, an enzyme that oxidizes or reduces glucose, such as glucose oxidase, dehydrogenase, or reductase, and a redox mediator. Reduced mediator is oxidized at one of the electrodes, and electrochemical balance is maintained by a reducing reaction at the other electrode to result in a measurable current. The measured current is related to the concentration of glucose in the sample, and various techniques are known for determining glucose concentrations in such a system. (See, for example, U.S. Pat. Nos. 6,284,125; 5,942,102; 5,352,2,351; and 5,243,516, which are incorporated herein by reference.)

Determination of glucose or other analytes in a sample can also be made using other electrochemical techniques. These include potentiometry, for example as described in U.S. Pat. No. 6,251,260, which is incorporated herein by reference, or coulometry, for example as described in U.S. Pat. No. 6,299,757 which is incorporated herein by reference.

In one embodiment, a method for determining analyte in a sample in contact with two electrodes within a sample space of an electrochemical test strip is provided. The test strip has characteristic information encoded thereon prior to introduction of a sample. The method comprises the steps of:
(a) introducing sample to the sample space so that the sample is in contact with two electrodes within the sample space;
(b) determining a value that is representative of the double layer capacitance or the equivalent capacitance of the test strip; and
(c) translating the value determined in step (b) into information reflecting a characteristic of the test strip prior to introduction of sample,
(d) determining analyte in the sample disposed within the sample space, and
(e) using the characteristic information translated in step (c) to modify a result of step (d).

Step (c) occurs after step (b), however step (d) can occur before or after either of steps (b) or (c).

Apparatus of the Invention

The method of the invention can be used with any strip that has at least two electrodes provided a meter apparatus can receive the strip and provide the necessary applications of voltage and signal processing. Such a meter also forms an aspect of the present invention. Thus, the invention provides a meter for receiving an electrochemical test strip having electrodes and providing a determination of an analyte in a sample applied to the electrochemical test strip when received in the meter, said meter comprising:
(a) a housing having an opening for receiving an electrochemical test strip, said test strip having characteristic information encoded thereon;
(b) communications means for communicating a result to a user; and
(c) circuitry and a processor for making a determination of double layer capacitance or equivalent capacitance on a test strip having two electrodes within a sample space containing sample received within the meter; circuitry and a processor for translating the determined double layer capacitance or equivalent capacitance into information reflecting a characteristic of the test strip prior to introduction of sample; and circuitry and a processor for determination of an analyte in a sample within the sample space of the test strip.

Figure 7:
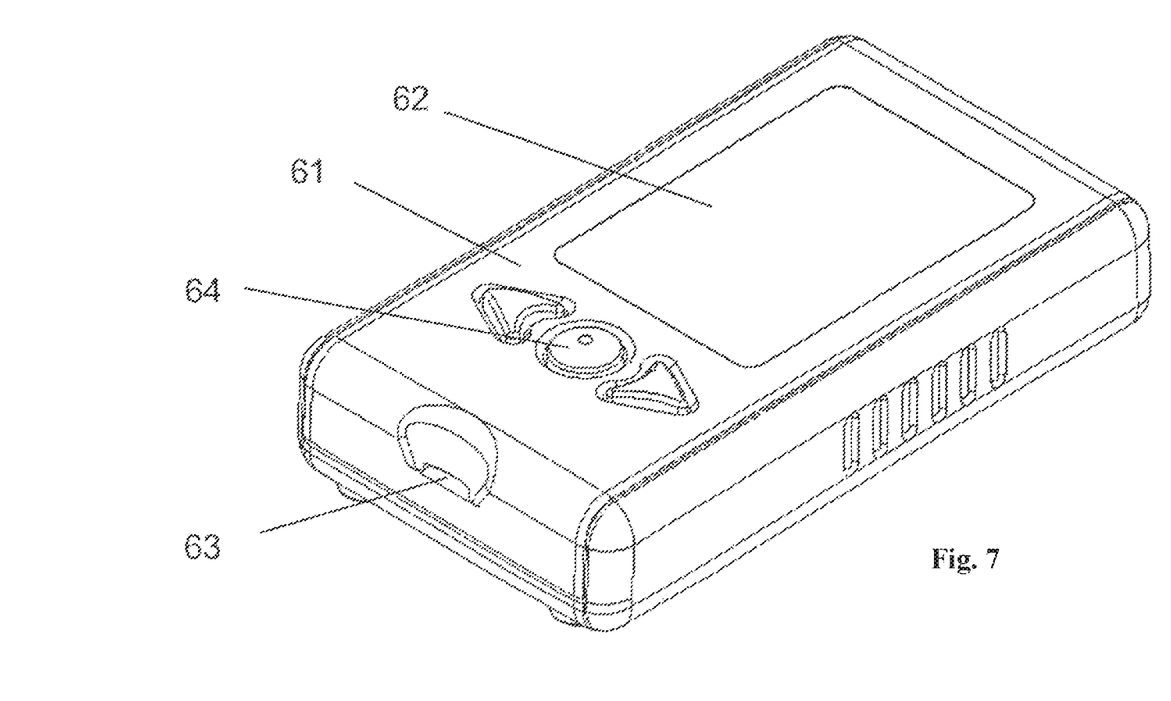
FIG. 7 shows an external view of a meter in accordance with the invention.

FIG. 7 shows an external view of a meter in accordance with the invention. The meter has a housing 61, and a display 62. The housing 61 has an opening 63, into which a test strip is inserted for use. The meter may also have a button 64 for signaling the start of the measurement cycle, or may have an internal mechanism for detecting the insertion of a test strip and/or the application of a sample. Such mechanisms are known in the art, for example from U.S. Pat. Nos. 5,266,179; 5,320,732; 5,438,271 and 6,616,819, which are incorporated herein by reference. In the meter of the invention, buttons, displays such as LCD displays, RF, infrared or other wireless transmitters, wire connectors such as USB, parallel or serial connections constitute means for receiving input from and communicating a result to a user, and can be used individually and in various combinations.

The meter of the present invention includes circuitry in the form of processor(s), software, and/or firmware, or any other type of instructions or circuitry capable of carrying out the method steps described above.

EXAMPLES

Obtaining Information from Test Strips—Example 1

An electrochemical meter is configured to determine the double layer capacitance of a test strip disposed within its test strip port. A control solution sample is introduced to two different test strips having different information encoded thereon as a result of having different effective electrode areas (e.g. strip 1–information 1/strip 2–information 2). It is determined that the control solution filled and sample space and completely covers two electrodes within the sample space. The double layer capacitance of both strips is determined and yield different values. These determined values are then translated (e.g. via reconciliation with a lookup table with known double layer capacitance ranges identifying the characteristic information) and the information encoded on the strips is determined to be strip 1–information 1/strip 2–information 2.

Obtaining Information from Test Strips—Example 2

An electrochemical meter is configured to determine the equivalent capacitance of a test strip disposed within its test strip port. A control solution sample is introduced to two different test strips having different information encoded thereon as a result of having different ionic salts present in the sample space (e.g. strip 1–potassium–information 1/strip 2-sodium-information 2). It is then determined that the control solution filled and sample space and completely covers two electrodes within the sample space. The equivalent capacitance of both strips is then determined and yields different values. These determined values are then translated (e.g. via reconciliation with a lookup table with known equivalent capacitance ranges with characteristic information) and the information encoded on the strips is determined to be strip 1-information 1/strip 2-information 2.

The invention claimed is:

1. A method for encoding characteristic information on a test strip, the test strip having only two electrodes and a double layer capacitance (DLC) when sample covers the electrodes in a sample space, the method comprising performing a step to control or alter a variable within the sample space which impacts the DLC,
wherein the step of controlling or altering the variable is performed during manufacture of the test strip and prior to introduction of sample to the sample space and such that the DLC falls within a predetermined range of values,
wherein the step to control or alter a variable within the sample space which impacts the DLC comprises a step selected from the group consisting of, controlling or altering the surface of either or both of the electrodes within the sample space of the test strip; and controlling or altering the material of construction of either or both of the electrodes within the sample space of the test strip;
thereby encoding characteristic information on the test strip;
wherein the characteristic information encoded on the test strip is information selected from the group consisting of: calibration information, regional or country coding, product identification, customer identification, assay type, and date of manufacture.

2. The method of claim 1, wherein the characteristic information is information reflecting a characteristic of the test strip at the time of manufacture of the test strip.

3. The method of claim 1, wherein the step of controlling or altering the variable comprises the step of controlling or altering the surface of either or both of the electrodes within the sample space of the test strip.

4. The method of claim 3, wherein a two-dimensional surface area, a three-dimensional surface area, and/or an effective area of the surface of the electrode is controlled or altered.

5. The method of claim 4, wherein the characteristic information is information reflecting a characteristic of the test strip at the time of manufacture of the test strip.

6. The method of claim 1, wherein the step to control or alter a variable comprises a step of controlling or altering the type and/or concentration of ions and/or mediator, wherein the ions and/or mediator are present in a reagent disposed within the sample space.

7. The method of claim 6, wherein the characteristic information is information reflecting a characteristic of the test strip at the time of manufacture of the test strip.

8. The method of claim 1, wherein the step to control or alter a variable comprises controlling or altering the material of construction of either or both of the electrodes within the sample space of the test strip.

9. The method of claim 8, wherein the characteristic information is information reflecting a characteristic of the test strip at the time of manufacture of the test strip.

* * * * *